US012290384B2

United States Patent
Pancoast et al.

(10) Patent No.: US 12,290,384 B2
(45) Date of Patent: May 6, 2025

(54) TWO-LAYER ADHESION OF ELECTRONICS TO A SURFACE

(71) Applicant: International Business Machines Corporation, Armonk, NY (US)

(72) Inventors: Leanna Pancoast, White Plains, NY (US); Katsuyuki Sakuma, Fishkill, NY (US)

(73) Assignee: International Business Machines Corporation, Armonk, NY (US)

( * ) Notice: Subject to any disclaimer, the term of this patent is extended or adjusted under 35 U.S.C. 154(b) by 346 days.

(21) Appl. No.: 17/823,168

(22) Filed: Aug. 30, 2022

(65) Prior Publication Data

US 2022/0409136 A1    Dec. 29, 2022

Related U.S. Application Data

(62) Division of application No. 16/665,254, filed on Oct. 28, 2019, now Pat. No. 11,471,105.

(51) Int. Cl.
*A61B 5/257*    (2021.01)
*A61B 5/00*    (2006.01)
(Continued)

(52) U.S. Cl.
CPC .......... *A61B 5/6832* (2013.01); *A61B 5/682* (2013.01); *A61B 5/6826* (2013.01); *A61L 31/06* (2013.01);
(Continued)

(58) Field of Classification Search
CPC .................................................. A61B 5/6832
See application file for complete search history.

(56) References Cited

U.S. PATENT DOCUMENTS 5,776,059 A  *  7/1998  Kaestle ............... A61B 5/411
                                                         600/340
2018/0085061 A1    3/2018  Heisig et al.
(Continued)

FOREIGN PATENT DOCUMENTS

WO    WO-2014/032193 A1  *  3/2014
WO    WO-2014/043158 A1  *  3/2014
WO       2018104574 A1     6/2018

OTHER PUBLICATIONS

Mascaro, Stephen Austin. "Design and analysis of fingernail sensors for measurement of fingertip touch fouce and finger posture." PhD diss., Massachusetts Institute of Technology, 2002.*
(Continued)

*Primary Examiner* — Jeffry H Aftergut
(74) *Attorney, Agent, or Firm* — CANTOR COLBURN LLP; Michael Petrocelli

(57) ABSTRACT

Embodiments of the present invention are directed to a two-layer adhesive and methods of using the same to secure an electronic device to an organism. In a non-limiting embodiment of the invention, a surface of the organism is coated with a first adhesive layer (bottom layer). The first adhesive layer is cured and a surface of the cured first adhesive layer is coated with a second adhesive layer (top layer). An electronic device is positioned on the second adhesive layer prior to curing the second adhesive layer. The second adhesive layer is then cured, thereby embedding the electronic device within the second adhesive layer. The bottom layer and the top layer are selected such that the bottom layer releases upon exposure to a first solvent after a first duration and the top layer releases upon exposure to a second solvent after a second duration more than the first duration.

17 Claims, 6 Drawing Sheets

(51) Int. Cl.
*A61L 31/06* (2006.01)
*A61L 31/14* (2006.01)
*C09J 5/06* (2006.01)
*C09J 7/10* (2018.01)

(52) U.S. Cl.
CPC ............... *A61L 31/141* (2013.01); *C09J 5/06* (2013.01); *C09J 7/10* (2018.01); *A61B 2503/40* (2013.01)

(56) References Cited

U.S. PATENT DOCUMENTS

| | | |
|---|---|---|
| 2018/0116594 A1 | 5/2018 | Heisig et al. |
| 2018/0165566 A1 | 6/2018 | Rogers |
| 2018/0271643 A1 | 9/2018 | Gunn et al. |
| 2018/0368961 A1 | 12/2018 | Shanjani et al. |
| 2019/0076334 A1 | 3/2019 | Alauddin et al. |
| 2019/0351262 A1 | 11/2019 | Landa et al. |
| 2021/0024785 A1 | 1/2021 | Nagar |
| 2021/0121128 A1 | 4/2021 | Pancoast et al. |
| 2022/0011493 A1 | 1/2022 | Bennett et al. |

OTHER PUBLICATIONS

Katsuyuki Sakuma et al., "Wearable Nail Deformation Sensing for Behavioral and Biomechanical Monitoring and Human-Computer Interaction," NATURE: Scientific Reports Journal, vol. 8, Article No. 18031, 2018; (11 pages).

List of IBM Patents or Patent Applications Treated as Related; Date Filed: Aug. 30, 2022, 2 pages.

* cited by examiner

TWO-LAYER ADHESION OF ELECTRONICS TO A SURFACE

BACKGROUND

The present invention relates generally to wearable, flexible, healthcare and medical related electronics. More specifically, the present invention relates to a two-layer adhesive for securing flexible wearable sensor electronics to a surface of a live organism, including, but not limited to, the organism's fingernails, toenails, teeth, claw, hoof, and skin.

The development of technologies that enable the wireless collection and analysis of quantitative, clinically relevant information on a patient's physiological status is of growing interest. In particular, soft, biocompatible systems are widely regarded as important because they facilitate the mounting of wearable sensors on external (e.g., skin or nail) and internal (e.g., heart and brain) surfaces of the body. Wearable sensors allow for the collection and analysis of clinically relevant information directly on the patient, and ultraminiaturized, lightweight, and battery-free wearable devices have the potential to establish complementary options in biointegration, where longer duration (e.g., months) interfaces are possible on hard surfaces such as the fingernails and the teeth, with negligible risk for irritation or discomfort. Some example wearable sensors include strain gauges, temperature sensors, accelerometers, photoplethysmograms (PPGs), electrocardiograms (ECGs), electroencephalography (EEG) devices, respiration sensors, gyroscopes, and piezoelectric sensors.

Strain gauges, for example, are useful for measuring or monitoring stresses, forces, torques and a host of other stimuli including displacement, acceleration and position of the patient's body. The electrical conductance of a strain gauge (typically formed of a doped silicon or metal) varies with its geometry, such that a deformation of the strain gauge results in a change in its electrical resistance. The stress on a strain gauge can therefore be inferred from a measured resistance of the strain gauge using a known gauge factor, which is a ratio of relative change is resistance to the strain on the test piece. The resistance of the strain gauge can be measured using a Wheatstone bridge.

Regardless of the specific type of wearable sensor used in a given application, an adhesive is typically applied at the interface between the patient and the sensor to bond these wearable sensors to the patient's body. For example, cyanoacrylate-based adhesives can ensure the strong adhesion of a strain gauge to a fingernail or toenail. Cyanoacrylates are popular adhesives for wearable sensors because they offer a fast drying, semi-permanent bond that can be easily and conformally coated over a portion of the patient's body, such as a fingernail.

SUMMARY

Embodiments of the invention are directed to a method for using a two-layer adhesive to secure an electronic device to a patient (e.g., to a live nail) or an animal (e.g., claw, hoof). A non-limiting example of the method includes coating a surface of the nail with a first adhesive layer (bottom layer). The first adhesive layer is cured and a surface of the cured first adhesive layer is coated with a second adhesive layer (top layer). An electronic device is positioned on the second adhesive layer prior to curing the second adhesive layer. The second adhesive layer is then cured, thereby embedding the electronic device within the second adhesive layer. The bottom layer and the top layer are selected such that the bottom layer releases upon exposure to a first solvent after a first duration and the top layer releases upon exposure to a second solvent after a second duration more than the first duration.

Embodiments of the invention are directed to a method for removing an electronic device from a patient (e.g., from a live nail). A non-limiting example of the method includes forming an adhesive stack on a surface of the patient. The adhesive stack can include a bottom layer positioned between a top layer and the surface of the patient. The electronic device can be embedded in the top layer. The bottom layer and the top layer are selected such that the bottom layer releases upon exposure to a first solvent after a first duration and the top layer releases upon exposure to a second solvent after a second duration more than the first duration. The method can include exposing the adhesive stack to the first solvent for the first duration to release the adhesive stack from the surface of the patient. The method can include removing the adhesive stack from the patient.

Embodiments of the invention are directed to an adhesive stack for securing an electronic device to a live nail. A non-limiting example of the adhesive stack includes a top layer and a bottom layer positioned between the top layer and a surface of the live nail. The adhesive stack can further include an electronic device embedded in the top layer. The bottom layer and the top layer are selected such that the bottom layer releases upon exposure to a first solvent after a first duration and the top layer releases upon exposure to a second solvent after a second duration more than the first duration.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
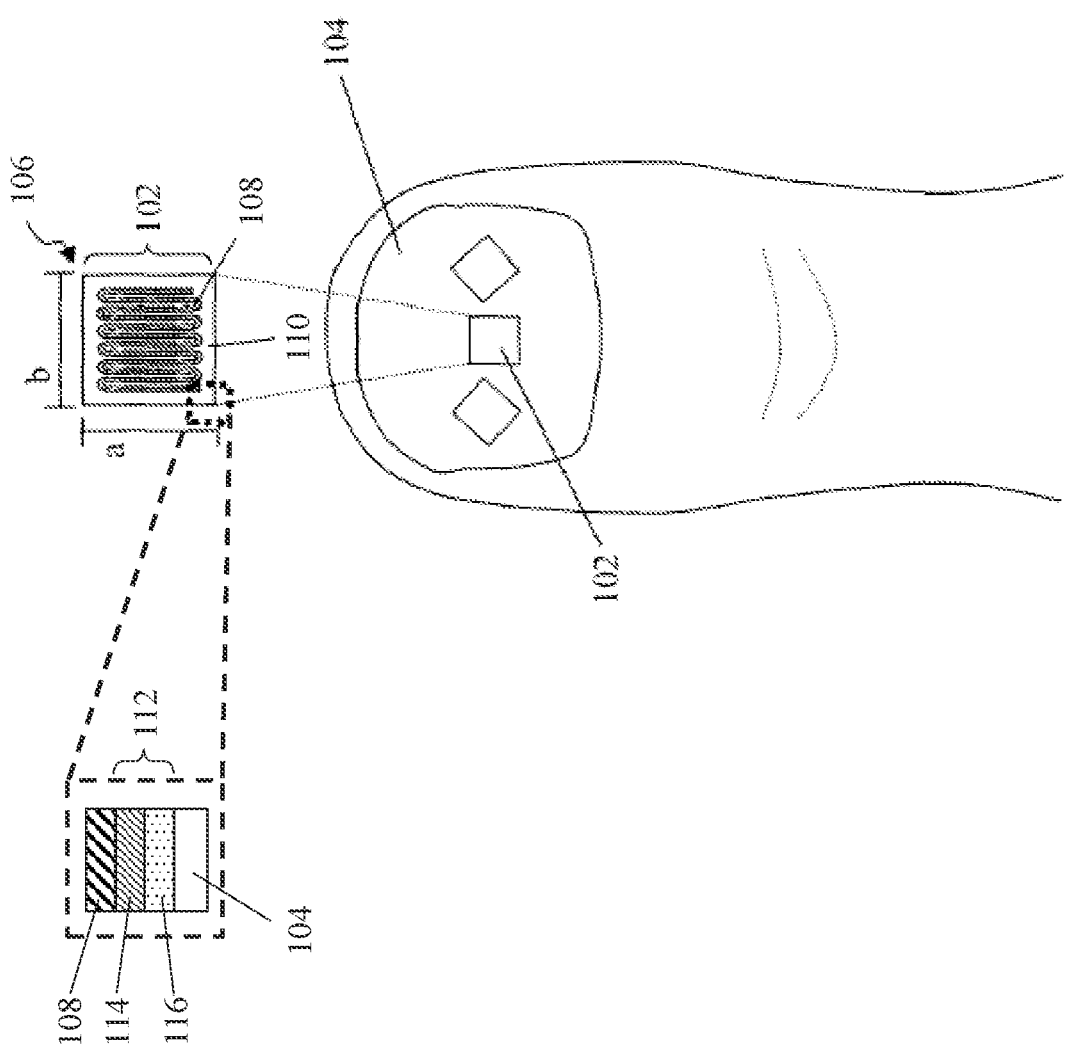
FIG. 1 depicts an electronic device attached to a body surface according to one or more embodiments of the invention.

The diagrams depicted herein are illustrative. There can be many variations to the diagram or the operations described therein without departing from the spirit of the invention. For instance, the actions can be performed in a differing order or actions can be added, deleted or modified.

In the accompanying figures and following detailed description of the described embodiments of the invention, the various elements illustrated in the figures are provided with two or three-digit reference numbers. With minor exceptions, the leftmost digit(s) of each reference number correspond to the figure in which its element is first illustrated.

DETAILED DESCRIPTION

It is understood in advance that although example embodiments of the invention are described in connection with a particular wearable sensor (e.g., a strain gauge), embodiments of the invention are not limited to the particular sensor architectures described in this specification. Rather, embodiments of the present invention are easily capable of being implemented to bond a wide range of wearable sensors, such as an accelerometers, photoplethysmograms (PPGs), electrocardiograms (ECGs), electroencephalography (EEG) devices, gyroscopes, temperature sensors, respiration sensors, piezoelectric sensors, heart-monitoring devices, glucose-monitoring devices, and TENS (transcutaneous electrical nerve stimulation) electrode therapy devices, among others, to a body surface of an organism, including, for example, the organism's fingernails, toenails, teeth, claw, hoof, and skin.

Turning now to an overview of technologies that are more specifically relevant to aspects of the present invention, an adhesive such as a cyanoacrylate is commonly used to bond wearable sensors (electronic devices such as strain gauges) to a patient's body (often a fingernail). An ideal adhesive needs to satisfy several criteria. First, an adhesive should be stiff enough to allow viable signals to be read by a sensor/monitor. In other words, the young's modulus of the adhesive material needs to be large enough to allow deformations to not be dampened. An adhesive should be strong, allowing for the wearable sensor to remain on the patient for as long as needed. To ease application and patient distress, the adhesive should cure or dry in as short a time as possible. Similarly, the patient's body should not need to be put into an awkward position during application, due to patient's comfort as well as an inability to stay still long enough to allow the application of the sensor. Finally, once the wearable sensor is no longer needed, the adhesive should be easily removable, without causing harm to the patient's body or to the sensor itself (for reusability or further study).

Cyanoacrylates are ubiquitous as medical device adhesives, particularly with respect to wearable sensors placed on a patient's fingernail, in part because the cyanoacrylate family satisfies so many characteristics of an ideal adhesive. Cyanoacrylates are fast drying (typically around 30 seconds) adhesives that can be conformally coated onto a patient's body to provide a strong, semi-permanent bond. As a result, many methods used to attach a sensor to a fingernail rely upon products whose main ingredient is cyanoacrylate.

Cyanoacrylates make excellent adhesives, but they are very difficult to remove. Cyanoacrylates are typically removed using mechanical force—scratching off, scoring, scraping, etc. While effective at removing a cyanoacrylate-based adhesive, these methods are slow, will damage a patient's nail or skin, and can destroy the wearable sensor. This results in harm to the patient and prevents reuse of the sensor. To mitigate the damage to the patient and to the electronics and to speed up the removal process, the interface between the patient and the wearable sensor can be soaked in a solvent to release the adhesive. Acetone is typically used as exposure to acetone will soften a dried cyanoacrylate.

Adhesive removal even with a solvent soak, however, can take up to 30 minutes or even longer (depending on thickness of application) before the adhesive fully releases from the nail. Oftentimes, repeat soakings in the solvent are needed. This removal process is impractically long and burdensome. In addition, a surface such as a fingernail provides a very limited contact area between the solvent with the adhesive, further increasing removal time and inconvenience. Even worse, prolonged soaks in solvents such as acetone can weaken a nail—resulting in the same type of damage to the nail that a solvent soak is trying to prevent.

Turning now to an overview of aspects of the present invention, one or more embodiments of the invention address the above-described shortcomings of the prior art by providing a new two-layer adhesive for securing electronics to a patient's body (nails, skin, teeth, etc.). This two-layer adhesive includes a top adhesive layer and a bottom adhesive layer. The top adhesive layer is a fast drying, permanent bonding material that secures the sensor. As used herein, a "permanent" bonding material includes adhesive materials that require mechanical force (scratching off, scoring, scraping, etc.) or long solvent soaks (greater than about 5 minutes) to remove. This top layer can include strong adhesives such as cyanoacrylates. The bottom adhesive layer is a fast drying, temporary bonding material that is applied directly to the patient's body (e.g., nail) and binds the top adhesive layer to the patient. As used herein, a "temporary" bonding material includes adhesive materials that can be peeled or wiped off without requiring a long solvent soak time (e.g., materials that can be removed after a solvent soak of less than about 5 minutes, or materials that do not required any solvent soak). In other words, the material for the bottom adhesive layer is selected to be easily removable, ensuring that the two-layer adhesive can be removed from the patient without resorting to damaging mechanical processes or prolonged soak periods (e.g., soaks greater than 5 minutes).

Advantageously, the bottom adhesive layer prevents the top adhesive layer from making direct contact with the patient's body. This allows for the use of conventionally strong adhesives (e.g., cyanoacrylates) without needing to worry about the difficult removal requirements of those adhesives. In other words, this two-layer adhesive inserts an easily removable temporary adhesion material between a strong, permanent bonding material and the patient's body. Once removed from the patient's body, the top adhesive layer and the sensor layer can be soaked in a solvent for separation and eventual reuse of the sensor layer (without patient aggravation).

Turning now to a more detailed description of aspects of the present invention, FIG. 1 depicts an electronic device 102 attached to a body surface (as shown, a fingernail 104) in accordance with one or more embodiments of the present invention. In some embodiments of the invention, multiple instances of the electronic device 102 are attached to the same or various body surfaces (e.g., to the same fingernail or to a combination of fingernails, toenails, teeth, skin, etc.), optionally at different orientations/locations. However, embodiments are contemplated herein where a single electronic device 102 is employed at a single location of a person's body.

In some embodiments of the invention, the electronic device 102 is a wearable sensor. For example, the electronic device 102 can be a strain gauge. In some embodiments of the invention, the electronic device 102 is an accelerometer, photoplethysmogram (PPG), electrocardiogram (ECG), electroencephalography (EEG), temperature sensor, respiration sensor, gyroscope, piezoelectric sensor, heart-monitoring device, glucose-monitoring device, TENS (transcutaneous electrical nerve stimulation) electrode therapy device, or any other type of wearable device. In some embodiments of the invention, the body surface is the fingernail 104. In some embodiments of the invention, the body surface is one or more of a patient's fingernails, toenails, teeth, or skin. Although the body surface depicted in FIG. 1 is a fingernail 104, the two-layer adhesion processes and resulting structures described in connection with the fingernail 104 apply equally to various body surfaces, including, for example, toenails, teeth, and skin.

As further shown in FIG. 1, the footprint of the electronic device 102 can be configured to fit on the respective body surface (e.g., 15 mm×15 mm or less for a human fingernail 104). For instance, in the present example, each sensor (electronic device 102) is smaller than the respective fingernail 104 to which it is attached, thereby enabling multiple sensors to be attached to the same fingernail 104. In some embodiments of the invention, the footprint (a×b) of the electronic device 102 is less than or equal to 15 mm×15 mm, although other sizes are within the contemplated scope of the invention. In other words, the configuration shown in FIG. 1 is merely an example, and the number, orientation, and size of the sensors can be adjusted (e.g., the footprints can be scaled up or down, etc.) depending on the particular application.

A magnified view 106 of the electronic device 102 is provided. In some embodiments of the invention, the electronic device 102 is a strain gauge sensor having multiple stacked layers. In some embodiments of the invention, the strain gauge sensor version of the electronic device 102 can include a metal sensor wire 108 placed over a flexible substrate 110. As will be described in detail below, embodiments of the invention are contemplated herein where the flexible substrate 110 includes a two-layer adhesive 112.

As further shown in FIG. 1, the metal sensor wire 108 can be configured to have a serpentine layout to increase the available length of the metal sensor wire 108, and hence the resistance. While a serpentine layout of the metal sensor wire 108 is shown, other configurations are possible. With the constraints on the overall footprint of the electronic device 102 (see above), the length of the sensor wire 108 can only be made so long. In some embodiments of the invention, to further increase the overall resistance, and thereby decrease the total current and power consumption of the sensor, multiple sensor layers are stacked (not shown). Interconnects can be used to electrically couple the stacked layers.

Figure 2:
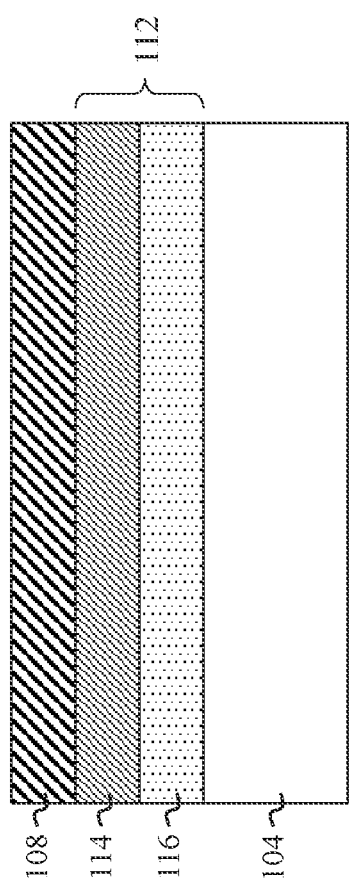
FIG. 2 depicts a cross-sectional view of the electronic device and the two-layer adhesive shown in FIG. 1 according to one or more embodiments of the invention.

FIG. 2 depicts a cross-sectional view of the electronic device 102 and the two-layer adhesive 112 shown in FIG. 1. As discussed previously herein, the electronic device 102 is built on a flexible substrate 110. The flexible substrate 110 can include the two-layer adhesive 112.

In some embodiments of the invention, the two-layer adhesive 112 can include a top adhesive layer 114 and a bottom adhesive layer 116. The top adhesive layer 114 can include a fast drying, permanent bonding material that secures the metal sensor wire 108. For example, the top adhesive layer 114 can include strong adhesives such as cyanoacrylates.

The bottom adhesive layer 116 can include a fast drying, temporary bonding material that is applied directly to the patient's body (e.g., fingernail 104). The bottom adhesive layer 116 binds the top adhesive layer 114 to the fingernail 104. As discussed previously herein, the material for the bottom adhesive layer 116 is selected to be easily removable, ensuring that the two-layer adhesive 112 can be removed from the patient without resorting to damaging mechanical processes or prolonged soak periods (e.g., soaks greater than 5 minutes). In some embodiments of the invention, the bottom adhesive layer 116 is selected from one of three classes of composite materials, described sequentially below.

In some embodiments of the invention, the bottom adhesive layer 116 includes a film former, plasticizer, and solubilizing agent (also referred to as a stabilizer). The film former, plasticizer, and solubilizing agent collectively define a first class of adhesive materials. In some embodiments of the invention, the film former can include polyurethane-35 or acrylic or vinyl pyrrolidone (VP) crosspolymer resins. In some embodiments of the invention, the plasticizer can include glycerine. In some embodiments of the invention, the solubilizing agent can include laureth-21. Forming the bottom adhesive layer 116 from a film former, plasticizer, and solubilizing agent in this manner results in the bottom adhesive layer 116 having an air dry time of about 30 to 300 seconds. Advantageously, a removal time of only about 3 to 120 seconds can be achieved using only a water soak. The bottom adhesive layer 116 can be removed after the water soak by peeling or rubbing.

In some embodiments of the invention, the bottom adhesive layer 116 includes a film former, chain transfer agent, and photoinitiator. The film former, chain transfer agent, and photoinitiator collectively define a second class of adhesive materials. In some embodiments of the invention, the film former can include acrylates copolymer. In some embodiments of the invention, the chain transfer agent can include pentaerythrityl tetra mercaptopropionate. In some embodiments of the invention, the photoinitiator can include trimethyl benzoyl diphenyl phosphine oxide. In some embodiments of the invention, the bottom adhesive layer 116 includes a film former, chain transfer agent, photoinitiator, plasticizer, and photosensitizer. The plasticizer can include, for example, dimethicone. The photosensitizer can include, for example, isopropyl thioxanthone. Forming the bottom adhesive layer 116 from a film former, chain transfer agent, and photoinitiator in this manner results in the bottom adhesive layer 116 having a UV-based dry time of about 60 seconds. Advantageously, a removal time of only about 3 to 120 seconds can be achieved using only a water soak. The bottom adhesive layer 116 can be removed after the water soak by peeling or rubbing.

In some embodiments of the invention, the bottom adhesive layer 116 includes a film former, solvent, and plasticizer. The film former, solvent, and plasticizer collectively define a third class of adhesive materials. In some embodiments of the invention, the film former can include nitrocellulose, tosylamide-based resins, or formaldehyde-based resins (e.g., tosylamide formaldehyde resin). In some embodiments of the invention, the solvent can include ethyl acetate, butyl acetate, propyl acetate, isopropyl alcohol, or diacetone alcohol. In some embodiments of the invention, the plasticizer can include trimethyl pentanyl diisobutyrate, triphenyl phosphate, ethyl tosylamide, or camphor. In some embodiments of the invention, the bottom adhesive layer 116 includes a film former, solvent, plasticizer, and diluent. The diluent can include, for example, dimethicone. Forming the bottom adhesive layer 116 from a film former, solvent, and plasticizer in this manner results in the bottom adhesive layer 116 having an air dry time of about 60 to 300 seconds.

Advantageously, a removal time of only about 10 to 120 seconds can be achieved using an acetone soak. The bottom adhesive layer 116 can be removed after the acetone soak by soaking or wiping.

Figure 3:
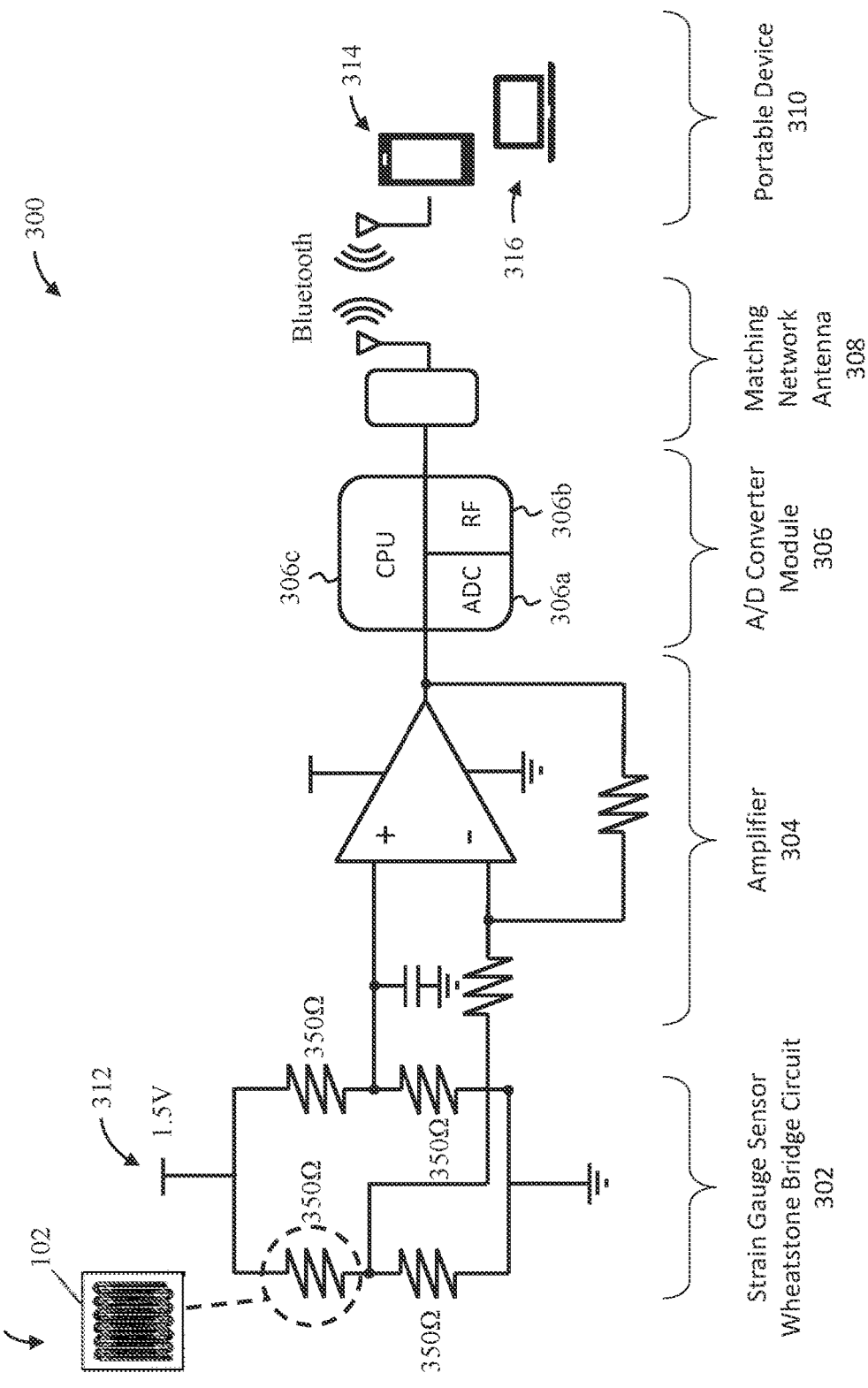
FIG. 3 depicts a system employing the electronic device shown in FIG. 1 according to one or more embodiments of the invention.

An exemplary system 300 employing the electronic device 102 attached to a patient via the two-layer adhesive 112 is depicted schematically in FIG. 3. In some embodiments of the invention, system 300 can include a strain gauge sensor and Wheatstone bridge circuit 302, an amplifier 304, an analog to digital converter module 306 that includes an analog to digital converter 306a (i.e., ADC), a radio frequency (RF) controller 306b and a micro-controller 306c, a network antenna 308, and a portable device 310. As further shown in FIG. 3, the electronic device 102 serves as a resistor in the Wheatstone bridge circuit 302. In some embodiments of the invention, the Wheatstone bridge circuit 302 receives power from power supply 312. It is notable that the values (i.e., power supply voltage, resistances, etc.) shown in FIG. 3 are merely given as examples and not intended to in any way limit the embodiments to these particular values.

Amplifier 304 serves to amplify the (voltage) signal output from the Wheatstone bridge circuit 302. Analog to digital converter 306a (i.e., ADC) in module 306 converts that amplified signal into a digital signal. Module 306 can also include a micro-controller 306c (e.g., a processor—CPU) that prepares (e.g., conditions, buffers, etc.) the signal for the radio frequency (RF) controller 306b that then transfers the digitized signals to a receiver.

Network antenna 308 transmits the digital signals from analog to digital converter 306. These digital signals are transmitted, for example, via near-field communication (NFC), WiFi, Bluetooth® technology, etc. to one or more user devices, such as a smartphone 314 (or other smart devices such as a smartwatch, smart glasses, etc.) and/or computer 316.

Figure 4:
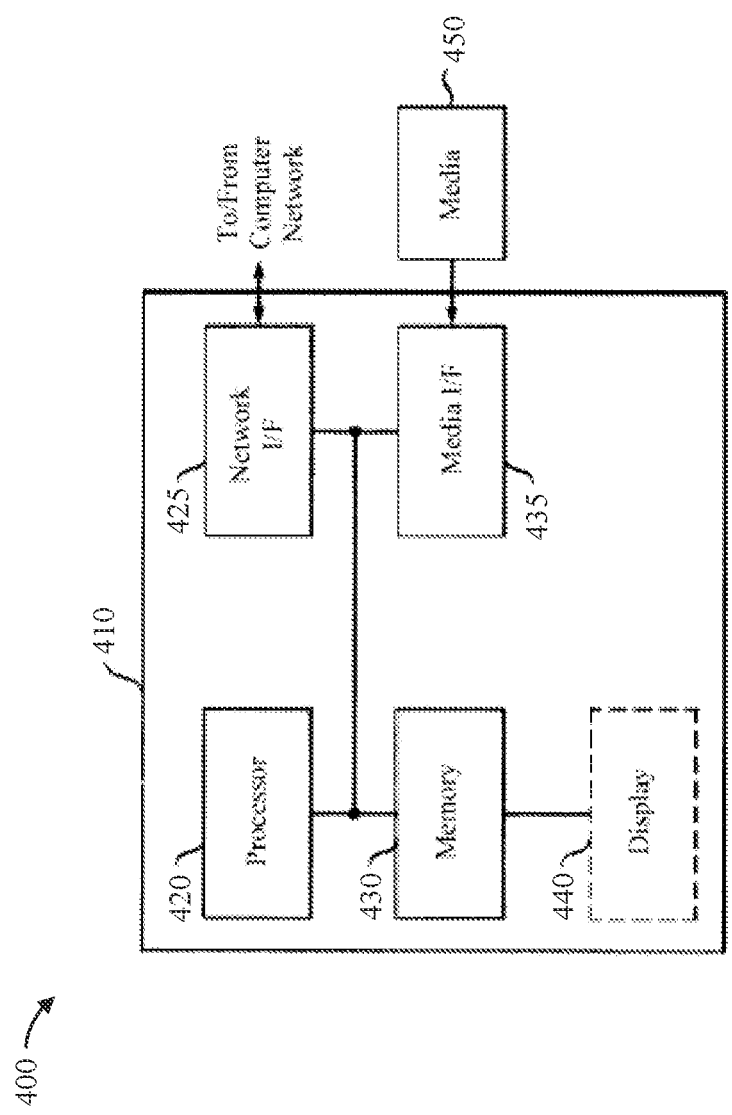
FIG. 4 depicts a block diagram for implementing the electronic device shown in FIG. 1 according to one or more embodiments of the invention.

Turning now to FIG. 4, a block diagram is shown of an apparatus 400 for implementing one or more of the techniques presented herein. By way of example only, apparatus 400 can be configured to serve as the micro-controller 306c and/or as one or more of the user devices (e.g., smartphone 314, computer 316, etc.) of system 300 (FIG. 3).

In some embodiments of the invention, apparatus 400 includes a computer system 410 and removable media 450. Computer system 410 includes a processor device 420, a network interface 425, a memory 430, a media interface 435 and an optional display 440. Network interface 425 allows computer system 410 to connect to a network, while media interface 435 allows computer system 410 to interact with media, such as a hard drive or removable media 450.

The processor device 420 can be configured to implement the methods, steps, and functions described herein. The memory 430 can be distributed or local and the processor device 420 could be distributed or singular. The memory 430 could be implemented as an electrical, magnetic or optical memory, or any combination of these or other types of storage devices. Moreover, the term "memory" should be construed broadly enough to encompass any information able to be read from, or written to, an address in the addressable space accessed by processor device 420. With this definition, information on a network, accessible through network interface 425, is still within memory 430 because the processor device 420 can retrieve the information from the network. It should be noted that each distributed processor that makes up processor device 420 generally contains its own addressable memory space. It should also be noted that some or all of computer system 410 can be incorporated into an application-specific or general-use integrated circuit.

In some embodiments of the invention, the optional display 440 can include any type of display suitable for interacting with a human user of apparatus 400. Generally, display 440 is a computer monitor, LCD or LED screen, or other similar display.

Figure 5:
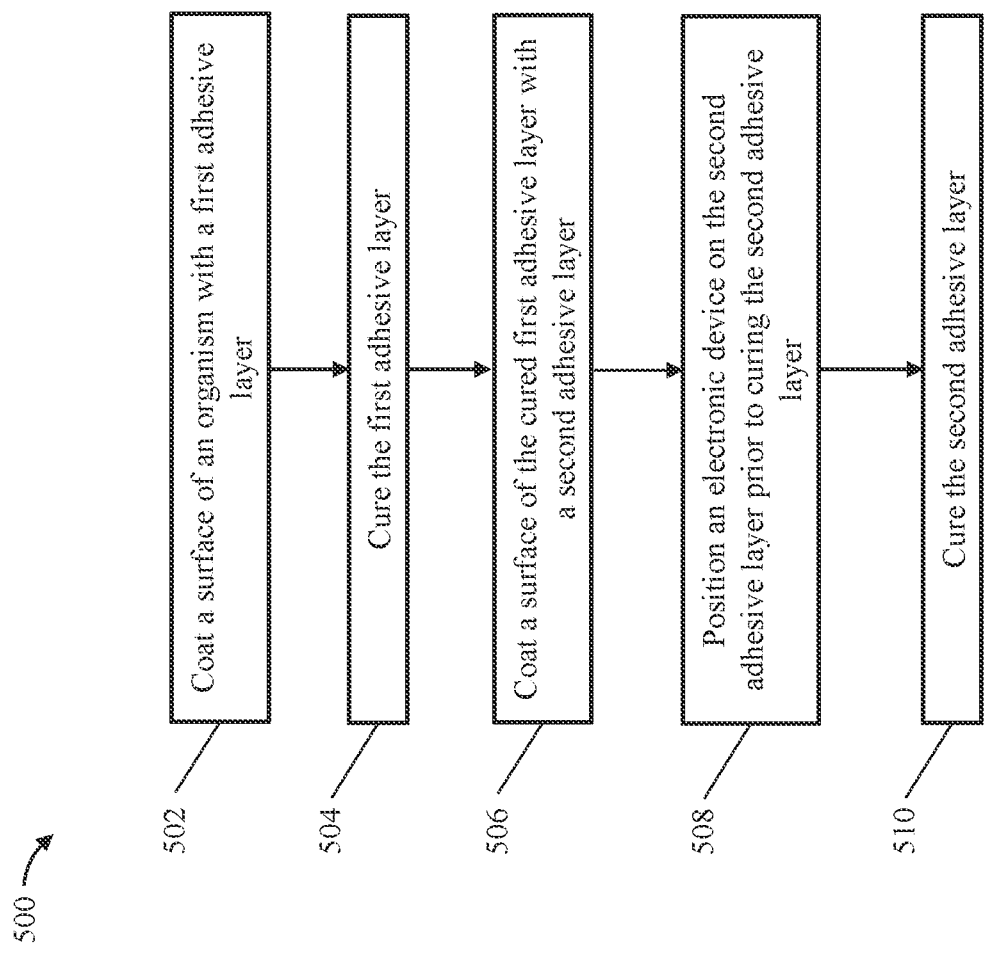
FIG. 5 depicts a flow diagram illustrating a method according to one or more embodiments of the invention.

FIG. 5 depicts a flow diagram 500 illustrating a method for securing an electronic device to a live nail using a two-layer adhesive according to one or more embodiments of the invention. As shown at block 502, a surface of the nail is coated with a first adhesive layer. In some embodiments of the invention, the first adhesive layer is selected from a first class of materials, a second class of materials, and a third class of materials.

In some embodiments of the invention, the first adhesive layer includes a film former, a plasticizer, and a solubilizing agent (collectively the first class of materials). In some embodiments of the invention, the film former includes one of polyurethane-35, acrylic crosspolymer resin, and vinyl pyrrolidone (VP) crosspolymer resin. In some embodiments of the invention, the plasticizer includes glycerine and wherein the solubilizing agent includes laureth-21.

In some embodiments of the invention, the first adhesive layer includes a film former, a chain transfer agent, and a photoinitiator (collectively the second class of materials). In some embodiments of the invention, the film former includes an acrylates copolymer, the chain transfer agent includes pentaerythrityl tetra mercaptopropionate, and the photoinitiator includes trimethyl benzoyl diphenyl phosphine oxide.

In some embodiments of the invention, the first adhesive layer includes a film former, a solvent, and a plasticizer (collectively the third class of materials). In some embodiments of the invention, the film former includes at least one of nitrocellulose, a tosylamide-based resin, or a formaldehyde-based resin. In some embodiments of the invention, the solvent includes one or more of ethyl acetate, butyl acetate, propyl acetate, isopropyl alcohol, and diacetone alcohol. In some embodiments of the invention, the plasticizer includes one or more of trimethyl pentanyl diisobutyrate, triphenyl phosphate, ethyl tosylamide, and camphor.

At block 504, the first adhesive layer is cured. In some embodiments of the invention, curing the first adhesive layer includes an air cure of about 30 to 300 seconds (e.g., for the first class of materials). In some embodiments of the invention, curing the first adhesive layer includes exposing the first adhesive layer to UV light for about 60 (e.g., for the second class of materials). In some embodiments of the invention, curing the first adhesive layer includes an air cure of about 60 to 300 seconds (e.g., for the third class of materials).

At block 506, a surface of the cured first adhesive layer is coated with a second adhesive layer. In some embodiments of the invention, the second adhesive layer includes cyanoacrylate.

At block 508, an electronic device is positioned on the uncured second adhesive layer (i.e., prior to curing the second adhesive layer). At block 510, the second adhesive layer is cured. In some embodiments of the invention, curing the second adhesive layer embeds the electronic device within the second adhesive layer or to the surface of the second adhesive layer. In some embodiments of the invention, the second adhesive layer is cured using an air cure of about 30 seconds, although other cure durations are within the contemplated scope of the invention depending on the particular material selected for the second adhesive layer.

Figure 6:
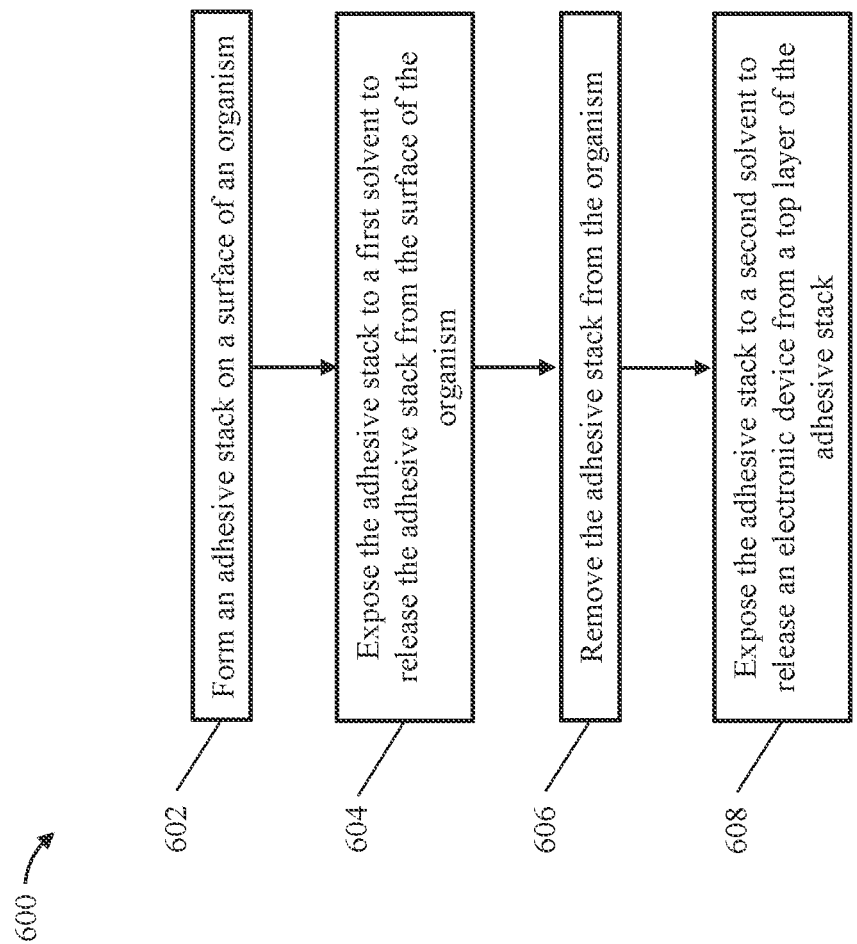
FIG. 6 depicts a flow diagram illustrating a method according to one or more embodiments of the invention.

FIG. 6 depicts a flow diagram 600 illustrating a method for removing an electronic device from a patient (e.g., a patient's live nail) using a two-layer adhesive according to one or more embodiments of the invention. As shown at block 602, an adhesive stack is formed on a surface of the patient.

In some embodiments of the invention, the adhesive stack releases upon exposure to a first solvent after a first duration and an electric device releases upon exposure to a second solvent after a second duration more than the first duration. For example, the bottom layer can be removed using water as a first solvent, and the cyanoacrylate top layer can be removed using acetone as the second solvent. In other words, the whole adhesive stack including the organism surface, bottom layer, top layer, and the electronic device will be exposed to the first solvent (e.g., water) for a set duration (e.g., 3 minutes). Exposure to the first solvent minimizes the amount of bottom layer material leftover and releases the remaining stack from the organism surface, exposing a discrete stack of top layer (e.g., cyanoacrylate) and the electronic device. The second solvent exposure releases the electronic device from the top layer. As discussed previously, in some embodiments of the invention, the second solvent exposure is done after separation from the organism and can include an arbitrarily longer duration than the first solvent exposure (e.g., 5 minutes, 10 minutes, 30 minutes, hours, etc.).

In some embodiments of the invention, the adhesive stack releases upon exposure to a first solvent (e.g., acetone) after a first duration and the electric device releases upon exposure to the first solvent (e.g., acetone) after a second duration more than the first duration. In other words, complete separation can be achieved using two soaks in the same solvent. For example, a relatively short soak in acetone can be used to remove the adhesive stack and electronic device from the surface of the organism, and a second, relatively longer soak in acetone can be used to remove the top layer from the electronic device.

In some embodiments of the invention, the electronic device is released from the adhesive stack prior to removal of the adhesive stack from the organism. In other words, in some embodiments of the invention, the adhesive stack is exposed to the second solvent prior to the first solvent.

In some embodiments of the invention, the top layer includes cyanoacrylate. In some embodiments of the invention, the bottom layer includes one or more of polyurethane-35, acrylic crosspolymer resin, vinyl pyrrolidone (VP) crosspolymer resin, an acrylates copolymer, nitrocellulose, a tosylamide-based resin, or a formaldehyde-based resin.

At block 604, the adhesive stack is exposed to the second solvent for the second duration to release the adhesive stack from the surface of the patient. At block 606, the adhesive stack is removed from the patient.

At block 608, after removing the adhesive stack, the adhesive stack is exposed to the second solvent for the second duration to separate the electronic device from the top layer. In some embodiments of the invention, the first solvent and the second solvent are the same. In some embodiments of the invention, the first solvent includes water and the second solvent includes acetone.

As can be seen from the foregoing detailed descriptions, technical effects and benefits of embodiments of the invention provide a new two-layer adhesive and methods of using the same to secure an electronic device to an organism (e.g., to a live nail of a patient). This new two-layer adhesive can be easily and quickly removed due to the inclusion of a temporary bottom layer, directly addressing the shortcomings of conventional adhesives (e.g., cyanoacrylate-based adhesives). Advantageously, the top layer of the two-layer adhesive can include conventionally strong, long lasting adhesives such as cyanoacrylates (for binding the electronic device), while the bottom layer can include an easily removable resin, such as one or more of polyurethane-35, acrylic crosspolymer resin, vinyl pyrrolidone (VP) crosspolymer resin, an acrylates copolymer, nitrocellulose, a tosylamide-based resin, or a formaldehyde-based resin.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Similarly, the term "coupled" and variations thereof describes having a communications path between two elements and does not imply a direct connection between the elements with no intervening elements/connections between them. All of these variations are considered a part of the specification. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

Spatially relative terms, e.g., "beneath," "below," "lower," "above," "upper," and the like, are used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device can be otherwise oriented (e.g., rotated 90 degrees or at other orientations), and the spatially relative descriptors used herein should be interpreted accordingly.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may include a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein

What is claimed is:

1. A method for removing an electronic device from an organism, the method comprising:
    forming an adhesive stack on a surface of the organism, the adhesive stack comprising a bottom layer positioned between a top layer and the surface of the organism, the electronic device embedded in the top layer, wherein the bottom layer releases upon exposure to a first solvent after a first duration and the top layer releases upon exposure to a second solvent after a second duration more than the first duration;
    exposing the adhesive stack to the first solvent for the first duration to release the adhesive stack from the surface of the organism; and
    removing the adhesive stack from the organism.

2. The method of claim 1, wherein the first solvent and the second solvent are the same.

3. The method of claim 1, wherein the second solvent comprises acetone and the first solvent comprises water.

4. The method of claim 1 further comprising, after removing the adhesive stack from the organism, exposing the adhesive stack to the second solvent for the second duration to separate the electronic device from the top layer.

5. The method of claim 1, wherein the top layer comprises cyanoacrylate and the bottom layer comprises one or more of polyurethane-35, acrylic crosspolymer resin, vinyl pyrrolidone (VP) crosspolymer resin, an acrylates copolymer, nitrocellulose, a tosylamide-based resin, or a formaldehyde-based resin.

6. The method of claim 1, wherein the surface of the organism is selected from the group consisting of a fingernail, a toenail, a tooth, a claw, a hoof, and an area of skin.

7. The method of claim 1, wherein the electronic device comprises at least one of a wearable sensor, a strain gauge, an accelerometer, a photoplethysmogram (PPG), an electrocardiogram (ECG), an electroencephalography (EEG), a temperature sensor, a respiration sensor, a gyroscope, a piezoelectric sensor, a heart-monitoring device, a glucose-monitoring device, and a transcutaneous electrical nerve stimulation (TENS) electrode therapy device.

8. The method of claim 1, wherein the bottom layer comprises:
    a film former;
    a plasticizer; and
    a stabilizer.

9. The method of claim 8, wherein the film former comprises one of polyurethane-35 and an acrylic or vinyl pyrrolidone (VP) crosspolymer resin, the plasticizer comprises glycerine, and the stabilizer comprises laureth-21.

10. The method of claim 9, wherein the first solvent comprises water and the first duration comprises 3 to 120 seconds.

11. The method of claim 1, wherein the bottom layer comprises:
    a film former;
    a chain transfer agent; and
    a photoinitiator.

12. The method of claim 11, wherein the film former comprises an acrylates copolymer, the chain transfer agent comprises pentaerythrityl tetra mercaptopropionate, and the photoinitiator comprises trimethyl benzoyl diphenyl phosphine oxide.

13. The method of claim 12, wherein the film former further comprises a plasticizer and a photosensitizer, wherein the plasticizer comprises dimethicone and the photosensitizer comprises isopropyl thioxanthone.

14. The method of claim 13, wherein the first solvent comprises water and the first duration comprises 3 to 120 seconds.

15. The method of claim 1, wherein the bottom layer comprises:
    a film former;
    a solvent; and
    a plasticizer.

16. The method of claim 15, wherein the film former comprises at least one of nitrocellulose, a tosylamide-based resin, and a formaldehyde-based resin, the solvent comprises at least one of ethyl acetate, butyl acetate, propyl acetate, isopropyl alcohol, and diacetone alcohol, and the plasticizer comprises at least one of trimethyl pentanyl diisobutyrate, triphenyl phosphate, ethyl tosylamide, and camphor.

17. The method of claim 16, wherein the first solvent comprises acetone and the first duration comprises 10 to 120 seconds.

\* \* \* \* \*